United States Patent [19]

Finke et al.

[11] Patent Number: 5,087,748
[45] Date of Patent: Feb. 11, 1992

[54] PROCESS FOR THE CONTINUOUS OLIGOMERIZATION OF HEXAFLUOROPROPENE OXIDE

[75] Inventors: Manfred Finke, Kelkheim; Günter Siegemund, Hofheim am Taunus; Heinz Strutz, Frankfurt am Main, all of Fed. Rep. of Germany

[73] Assignee: Hoechst Aktiengesellschaft, Frankfurt am Main, Fed. Rep. of Germany

[21] Appl. No.: 463,391

[22] Filed: Jan. 11, 1990

[30] Foreign Application Priority Data

Jan. 14, 1989 [DE] Fed. Rep. of Germany ........ 3901001

[51] Int. Cl.$^5$ .............................................. C07C 51/58
[52] U.S. Cl. ................................................... 562/851
[58] Field of Search ........................................ 562/851

[56] References Cited

FOREIGN PATENT DOCUMENTS 203466 3/1986 European Pat. Off. .

Primary Examiner—Paul J. Killos

[57] ABSTRACT

A continuous process for the preparation of perfluorinated carbonyl fluorides from hexafluoropropene oxide (HFPO), in which HFPO is continuously oligomerized in a catalyst solution in devices which allow separation of the heavy product phase from the catalyst phase during the reaction, is described. Different oligomer distributions can be achieved by choice of the catalyst and different operating temperatures. The reaction itself takes place always in the substantial absence of the product which is formed, and achieves a considerable saving in time.

8 Claims, No Drawings

PROCESS FOR THE CONTINUOUS OLIGOMERIZATION OF HEXAFLUOROPROPENE OXIDE

DESCRIPTION

The invention relates to a process for the continuous preparation of oligomers of hexafluoropropene oxide (HFPO).

The catalyzed oligomerization of HFPO has been disclosed [Angew. Chem. (1985) 97, 164]. It is carried out discontinuously in a stirred vessel or stirred autoclave, with HFPO being passed in, while stirring, until a particular level of the contents in the stirred vessel is reached. A period without agitation is then necessary, where appropriate while cooling the reaction mixture, in order to allow a phase separation of the light catalyst phase and the heavy product phase. Precise phase separation is, on the one hand, necessary in order that as little as possible of the catalyst, which is often costly, is carried out with the product and, on the other hand, the oligomeric acid fluorides should be contaminated as little as possible with the catalyst mixture or parts thereof in order to avoid possible problems in subsequent reactions or use of the HFPO oligomers. The discontinuous procedure, which is the technique hitherto practiced, is very elaborate and personnel-intensive and it leads, as a consequence of the necessity for a period without agitation and the fact that the reactor volume can often be utilized only inadequately, to small space-time yields and, owing to the unavoidable nonstationary state over long stretches, to variations in product quality.

The disadvantages can be eliminated by carrying out the oligomerization of HFPO continuously in the types of fluid-contact apparatus which allow, alone or in combination with additional apparatus, separation of the heavy product phase from the catalyst phase during the reaction.

Accordingly, the invention relates to a continuous process for the preparation of perfluorinated carbonyl fluorides of the formula

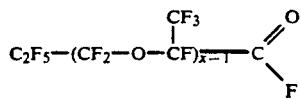

$$C_2F_5-(CF_2-O-CF)_{\overline{x-1}}-C\underset{F}{\overset{O}{\diagup\!\!\!\!\diagdown}} \quad (I)$$

in which x denotes an integer from 1 to 31, preferably 1 to 8, and in particular from 1 to 5, by catalyzed oligomerization of hexafluoropropene oxide (HFPO), entailing a reaction device which is composed of one or more reaction vessels and whose first vessel is equipped with an introduction device which is attached on the side in the lower third, with an appliance for controlling the level of the contents, and with a drainage device located at the bottom, being charged with a catalyst solution into which HFPO is fed continuously at a temperature of $-10$ to $+25°$ C. through the introduction device and is thereby converted into oligomers, entailing the mixture of catalyst solution and HFPO oligomers which have formed being separated into phases underneath the introduction device, or after transfer into another reaction vessel, and the catalyst phase optionally being returned into the reaction vessel, and the heavier product being removed through the drainage device located at the bottom of the reaction system.

Reaction devices of this type, called fluid-contact apparatuses, are described, for example, in Ullmanns Encyklopädie der technischen Chemie [Encyclopedia of Industrial Chemistry], 4th edition, volume 3, pages 357 et seq., Verlag Chemie 1973.

Examples which can be employed are stirred reactors or stirred vessel cascades, as long as these are connected to a separator and it is ensured, by measures of reaction technology, that the mixture of catalyst phase and product phase reaches the next reaction vessel or the separator. The two phases are separated in the separator which is of adequate size; the catalyst phase is returned, where appropriate, into the stirred vessel or the cascade, and the product phase is transferred to a storage vessel. A liquid-seal pump or a tubular reactor can be employed analogously.

Countercurrent reactors are preferred, such as, for example, bubble-cap or sieve-plate reactors, packed columns or reactors resembling spray towers. In these cases, the catalyst solution is fed in at the top, and the countercurrent of HFPO is passed in at the bottom. The catalyst and product phases run downwards and are collected underneath the HFPO inlet and separated into the phases. The upper phase (catalyst phase) is drawn off and returned to the reactor at the top. The heavy phase (product phase) is drained into a storage vessel.

The reaction vessel is equipped with an appliance for controlling the level of the contents, which ensures that the product phase which is located in the lower part does not rise above the level of the introduction device. It is ensured in this way that the HFPO is always introduced directly into the catalyst phase.

A particularly preferred fluid-contact apparatus is a bubble column, loop reactor or jet tube reactor, in which the gaseous or liquid HFPO is advantageously passed into the catalyst solution above the phase boundary between catalyst solution and product; the product which is formed sinks downwards, owing to gravity, through the catalyst phase and is separated, in a non-agitated zone below the metering-in point, into a separate phase and continuously drained into a storage vessel. HFPO can be metered in as gas or liquid.

HFPO oligomerization is an exothermal reaction. The heat which is produced can be removed by a jacket cooler, incorporated heat exchanger or by an external heat exchanger through which the catalyst solution is circulated during the reaction.

Finally, in the case of the preparation of short-chain oligomers of the formula (I) (x=1, 2, 3, 4), evaporative cooling is also possible by continuously taking off the short-chain oligomers (especially when x=1) at the top.

It is possible, where appropriate, for catalyst solution to be subsequently metered, from a storage vessel, continuously or discontinuously, into the actual reactor in order to replace catalyst which has been carried out and/or to allow partial exchange of catalyst during the reaction.

It is possible to employ as catalysts known systems, for example silver nitrate in polar organic solvents (DE-A 20 26 669), CuCl/CuCl$_2$/acrylonitrile/acetonitrile (DE-A 29 24 385), KF/adiponitrile/acetonitrile, CsF/tetraethylene diglycol ethers, but preferably N,N,N',N,-tetramethylethylenediamine/acetonitrile alone or with added CuCl (see DE-A 39 01 000.7 of the same date, entitled "A process for the oligomerization of hexafluoropropene oxide"), as long as the catalyst has, advantageously, a high activity and a long useful life and allows rapid and substantial phase separation. A high activity is desired in order to ensure complete reaction of the HFPO which is fed in.

HFPO oligomerization results in different oligomer distributions depending, in general, on the type of catalyst and operating temperature. These criteria also apply to the discontinuous procedure. However, it should be emphasized that the process according to the invention is suitable both for the continuous oligomerization of HFPO to give acid fluorides of the formula (I) with the emphasis on selectivity for (I) ($x=2$) and for the continuous oligomerization to give higher acid fluorides (I) ($x=3$ to 8).

The advantage of the fluid-contact apparatus employed according to the invention for the oligomerization of HFPO is that a continuous procedure is possible by allowing separation out of the oligomerization product, and thus a low concentration of the product which is formed in the catalyst phase, during the oligomerization. This ensures that the reaction always takes place in the substantial absence of the product which is formed, and this is associated with a considerable saving in time so that it is possible to employ smaller and simpler reaction apparatus which has no movable parts, for example stirring devices.

The procedure is simple and easy to carry out and thus less personnel-intensive. Moreover, the quasi-stationary state during the continuous oligomerization means that there are fewer variations in product quality.

Higher HFPO oligomers, in particular the trimer, tetramer and pentamer of HFPO, are used, for example, as building blocks for the preparation of perfluorinated inert liquids. The dimer of HFPO is used, inter alia, as intermediate for the preparation of perfluorinated propyl vinyl ether.

EXAMPLE 6 liters of a catalyst solution which is composed of 5.2 liters of dry acetonitrile, 755 ml of dry N,N,N',N,-tetramethylethylenediamine and 20 ml of water are introduced under protective gas into a bubble column (stainless steel; jacket cooler; internal diameter of the bubble column $=11$ cm). At 10 to 12° C., 6 kg of HFPO per hour are introduced through a sintered metal frit attached on the side of the column in the lower third. The resulting HFPO oligomers collect in a non-agitated zone below the metering-in frit. When the product phase has reached the device controlling the level of the contents, which is located below the metering-in frit, the HFPO oligomer phase is continuously drained through a valve located at the lower end of the bubble-column reactor. After the catalyst solution has reached the control mark it has an effective height $h_{eff}$ of 62 cm ($h_{eff}$=distance between gas-inlet frit and catalyst surface during operation). The conversion is greater than 99%, for example, after 158 kg of HFPO have been passed in, the following oligomer distribution of the compound (I) is found (in % by mass):

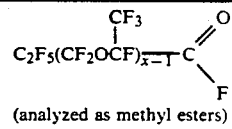

(analyzed as methyl esters)

| | S % by mass |
|---|---|
| $x=1$ | 15.00 |
| $x=2$ | 80.54 |
| $x=3$ | 4.46 |

We claim:

1. A process for the continuous preparation of perfluorinated carbonyl fluorides of the formula

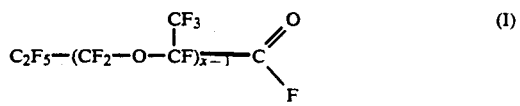

in which x denotes an integer from 1 to 31, comprising a catalyzed oligomerization of hexafluoropropene oxide (HFPO), entailing a reaction device which is composed of one or more reaction vessels and whose first vessel is equipped with an introduction device which is attached on the side in the lower third, with an appliance for controlling the level of the contents, and with a drainage device located at the bottom, the reaction device being charge with a catalyst solution allows structural phase separation and catalyzes the oligomerization process of HFPO into which HFPO is fed continuously at a temperature of $-10°$ C. to $+25°$ C. through the introduction device and is thereby converted into oligomers, entailing the mixture of catalyst solution and HFPO oligomers which have formed being continuously separated into phases underneath the introduction device, or after transfer into another reaction vessel, and the heavier product phase being continuously removed through the drainage device located at the bottom of the reaction system.

2. The process as claimed in claim 1, wherein the catalyst phase is returned into the reaction vessel.

3. The process as claimed in claim 1, wherein the reaction is carried out at temperatures from 5 to 15° C.

4. The process as claimed in claim 1, wherein gaseous or liquid HFPO is fed in.

5. The process as claimed in claim 1, wherein countercurrent reactors or fluid-contact units are employed in the reaction device.

6. The process as claimed in claim 5, whereby bubble-cap or sieve-plate reactors, packed columns, reactors resembling spray towers, or bubble columns, loop reactors or jet tube reactors are employed.

7. The process as claimed in claim 1, wherein catalyst solution is subsequently metered in continuously or discontinuously.

8. The process as claimed in claim 1, wherein a mixture of N,N,N', N-tetramethylethylenediamine/acetonitrile, alone or with added CuCl, is employed as catalyst solution.

* * * * *

UNITED STATES PATENT AND TRADEMARK OFFICE
CERTIFICATE OF CORRECTION

PATENT NO. : 5,087,748
DATED : February 11, 1992
INVENTOR(S) : Manfred Finke, et al.

It is certified that error appears in the above-indentified patent and that said Letters Patent is hereby corrected as shown below:

Column 2, line 63, the formula should read --N,N, N',N'-- --.
Column 3, line 43, the formula should read --N,N, N',N'- --.
Column 4, line 60, the formula should read --N,N,N',N'- --.

Signed and Sealed this

Ninth Day of November, 1993

Attest:

BRUCE LEHMAN

Attesting Officer     Commissioner of Patents and Trademarks